United States Patent [19]

Hinzmann

[11] Patent Number: 4,836,587
[45] Date of Patent: Jun. 6, 1989

[54] APPARATUS FOR MAKING KNOTS IN DRAWSTRINGS OF CATAMENIAL TAMPONS

[75] Inventor: Alfred Hinzmann, Weems, Va.

[73] Assignee: Hauni Richmond, Inc., Richmond, Va.

[21] Appl. No.: 137,511

[22] Filed: Dec. 23, 1987

[51] Int. Cl.[4] ............................................. B65H 69/04
[52] U.S. Cl. ........................................ 289/2; 28/120; 289/16.1
[58] Field of Search ............... 28/120; 289/2, 17, 18.1

[56] References Cited

U.S. PATENT DOCUMENTS

| | | | |
|---|---|---|---|
| 1,481,754 | 1/1924 | Stalson | 289/17 |
| 2,913,270 | 11/1959 | Sachenroder | 289/2 |
| 3,490,801 | 1/1970 | Feighery | 289/2 |
| 3,814,469 | 6/1974 | Simon | 28/120 X |
| 3,868,133 | 2/1975 | Franzen | 289/2 |
| 3,970,022 | 7/1976 | Kopatz et al. | 289/18.1 X |
| 4,490,894 | 1/1985 | Friese | 28/120 |

FOREIGN PATENT DOCUMENTS 1031305  8/1971  Canada ................................. 28/120

Primary Examiner—Louis K. Rimrodt
Attorney, Agent, or Firm—Peter K. Kontler

[57] ABSTRACT

One end of a drawstring which is connected to a catamenial tampon at the other end is pulled downwardly by suction while an intermediate portion of the drawstring is convoluted around a hollow mandrel to form a closed loop. The one end of the drawstring is then drawn into the mandrel by suction to convert the loop into a relatively loose knot which is or can be tightened by exerting a pull by suction upon the one end while and after the convoluted portion of the drawstring is stripped off the mandrel.

9 Claims, 4 Drawing Sheets

Fig. 1
Fig. 2
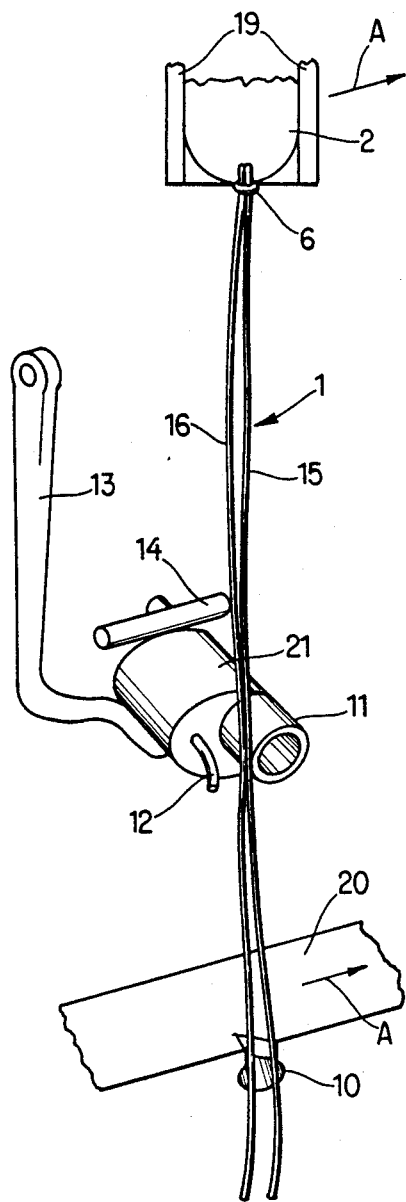
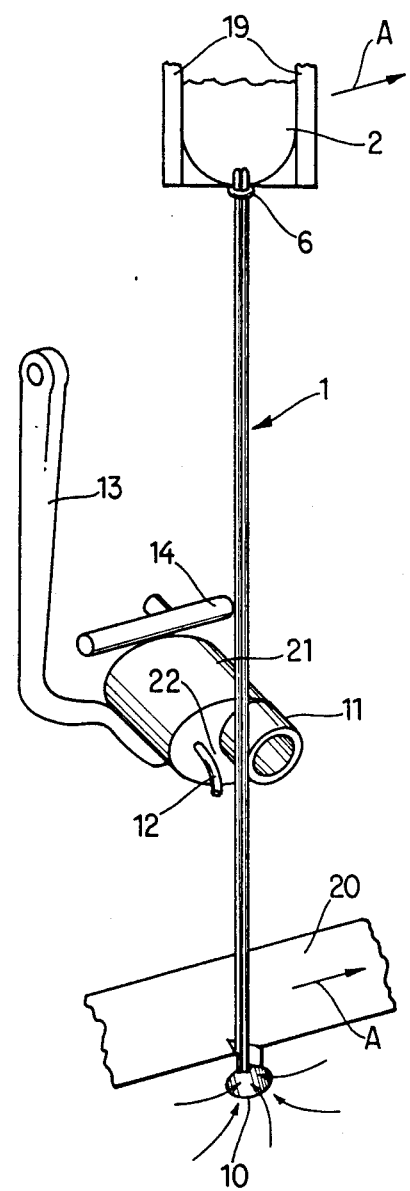

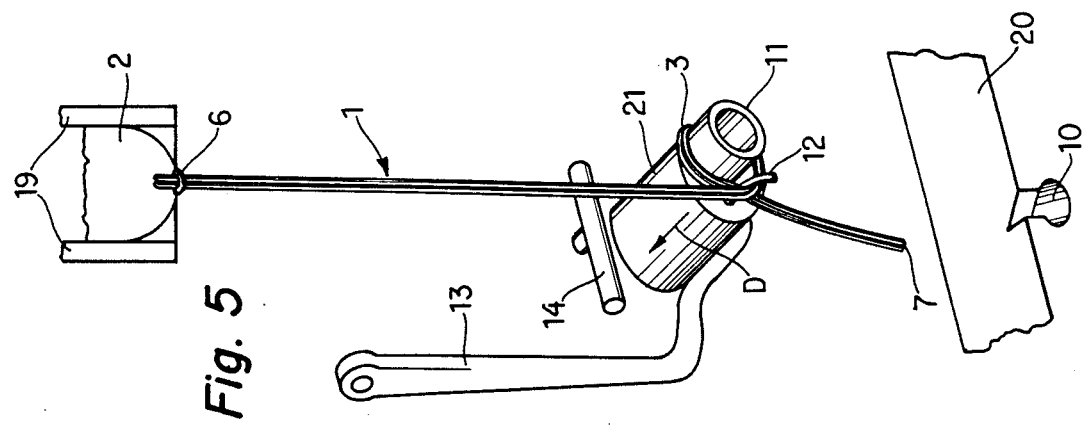
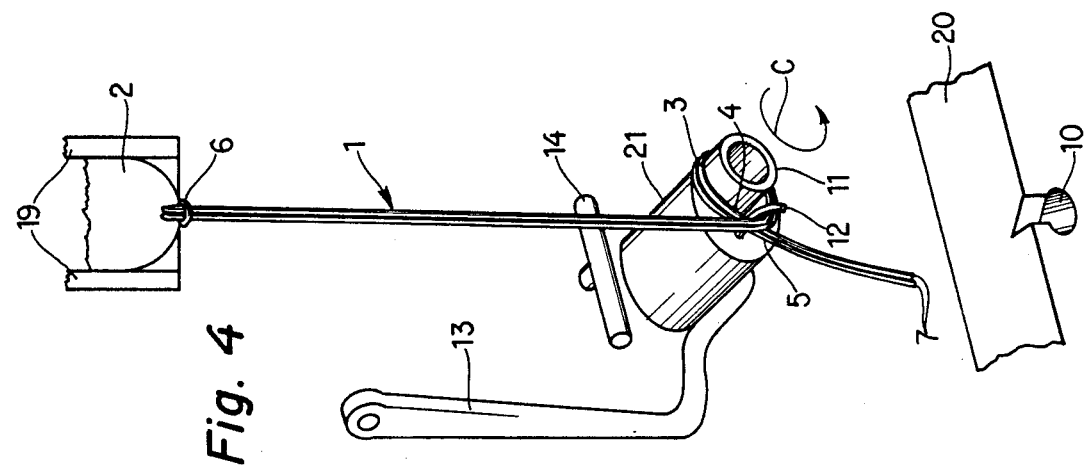
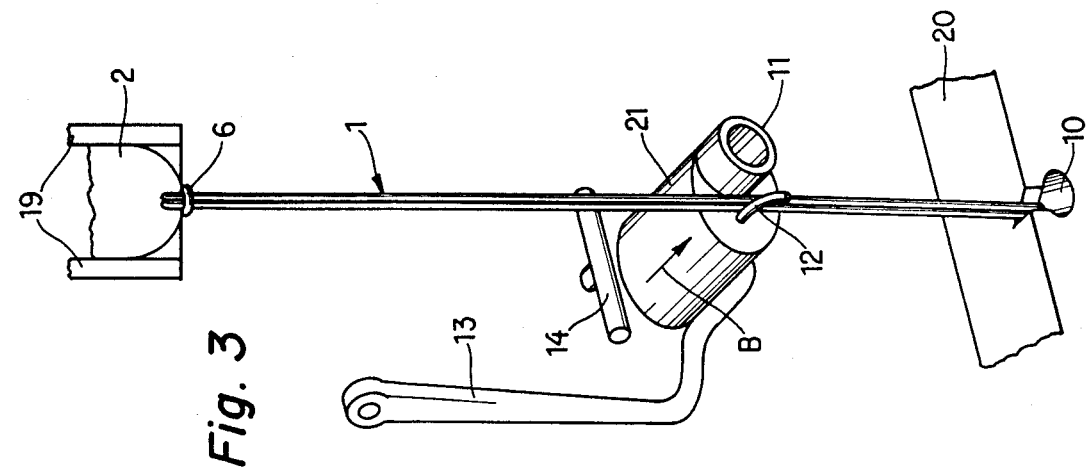

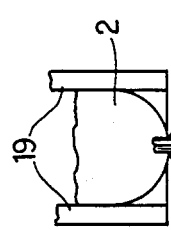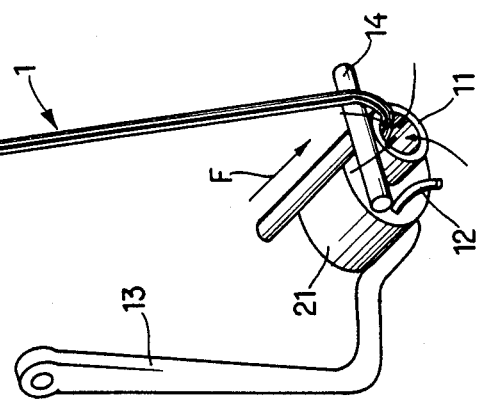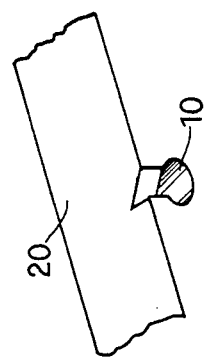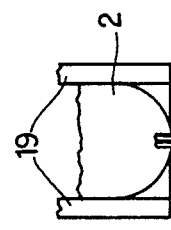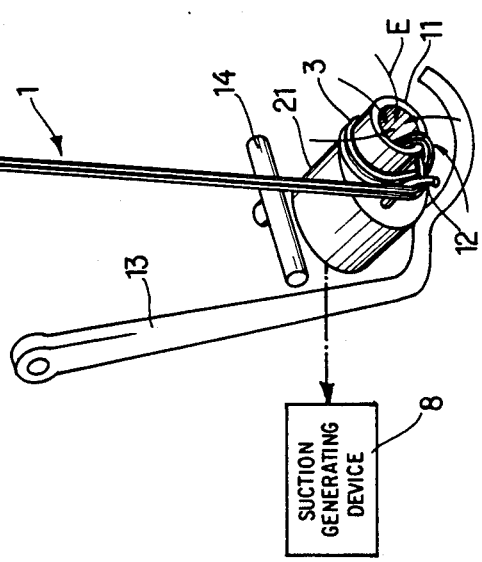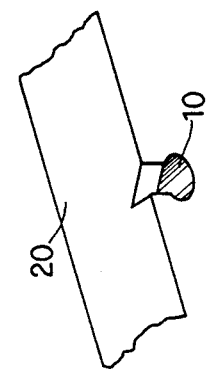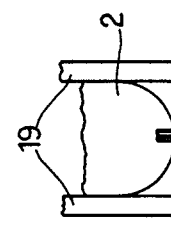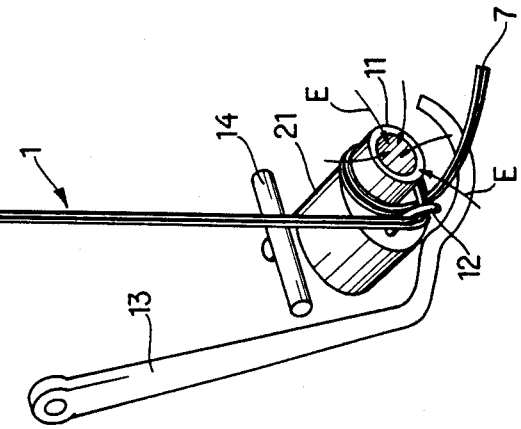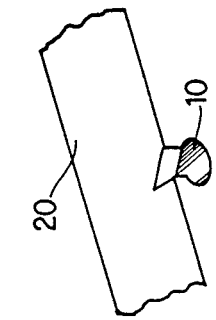

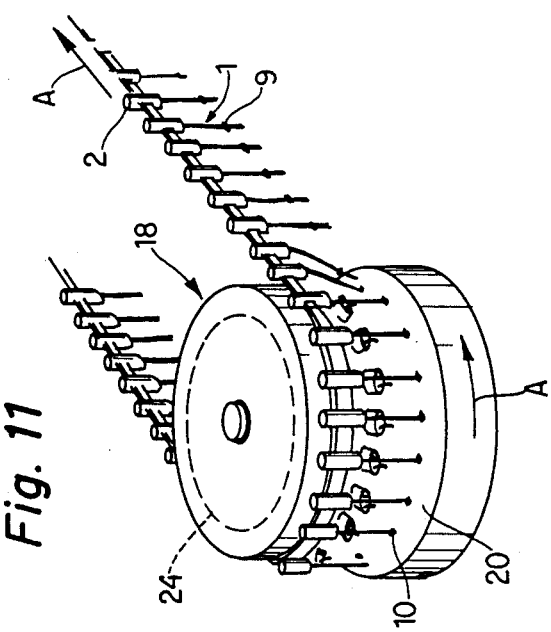
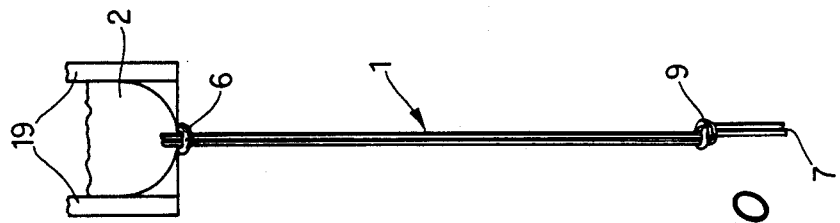
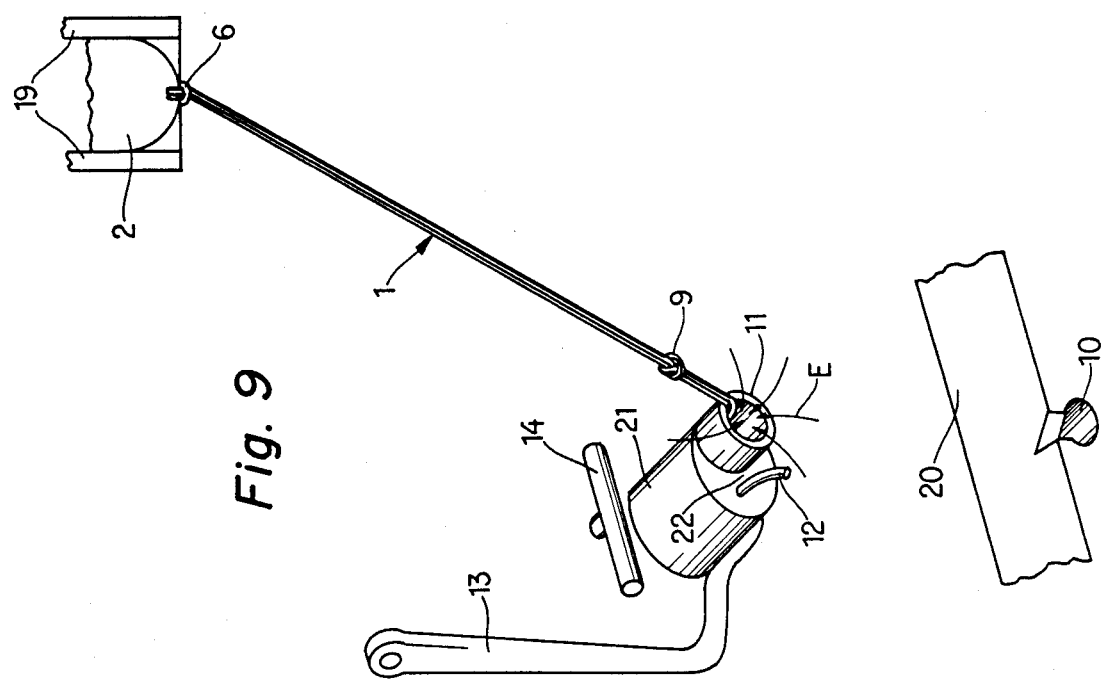

APPARATUS FOR MAKING KNOTS IN DRAWSTRINGS OF CATAMENIAL TAMPONS

BACKGROUND OF THE INVENTION

The invention relates to improvements in apparatus for making knots in flexible elements, particularly in so-called withdrawal strings, pull strings or drawstrings of catamenial tampons. More particularly, the invention relates to improvements in apparatus for making knots at a high frequency such as is required in connection with the production of tampons, tea bags and other mass-produced articles which are provided with strings or analogous flexible elements for convenience of manipulation. The invention will be described primarily with reference to the making and manipulation of catamenial tampons with the understanding, however that the apparatus can be used with equal or similar advantage for the making of knots in flexible elements which can be secured to a wide variety of commodities including tea bags as well as laces and many others.

It is well known to provide a catamenial tampon with a drawstring which facilitates extraction of the tampon and its disposal. It is also known to provide the drawstrings of tampons with knots so as to render it possible to more firmly engage the drawstring preparatory to and during extraction. Reference may be had, for example, to U.S. Pat. Nos. 4,543,098 (Wolfe et al.) and 3,762,413 (Hanke). A drawback of presently known methods of and apparatus for making such knots is that they are too slow and/or too unreliable. For example, the apparatus for making knots in the drawstrings of successive tampons can constitute a bottleneck in a production line which is designed to turn out hundreds of tampons per minute. Reference may be had to commonly owned U.S. Pat. No. 4,302,174 which discloses an automatic tampon making machine

OBJECTS AND SUMMARY OF THE INVENTION

An object of the invention is to provide a simple and inexpensive apparatus for making knots in flexible elements at a high frequency and with a high degree of predictability.

Another object of the invention is to provide an apparatus for making knots at the rate of several hundred per minute, for example, at the rate catamenial tampons are turned out by a modern high-speed production line.

A further object of the invention is to provide an apparatus which can make knots while the flexible elements are already attached to their carriers, such as tampons.

An additional object of the invention is to provide an apparatus which renders it possible to make knots in flexible elements each of which consists of two or more strands.

Still another object of the invention is to construct and assemble the apparatus in such a way that it can be readily installed in existing production lines for catamenial tampons as a superior substitute for heretofore known knot forming apparatus.

Another object of the invention is to provide the apparatus with novel and improved means for manipulating a series of successive flexible elements in the course of the knot forming operation.

A further object of the invention is to provide a machine, such as a tampon making machine, which embodies the above outlined apparatus.

An additional object of the invention is to provide the apparatus with novel and improved means for looping selected portions of flexible elements.

Another object of the invention is to provide the apparatus with novel and improved means for tightening the knots.

A further object of the invention is to provide a flexible element which is provided with a knot in the above outlined apparatus. The invention resides in the provision of an apparatus for making a knot in a flexible element, such as the drawstring or pull string of a catamenial tampon. The apparatus comprises means for forming in the flexible element a closed loop between the ends of the flexible element including means for overlapping two intermediate portions of the flexible element, means for pneumatically threading one end of the flexible element through the loop to thus form a relatively loose knot, and means for tightening the knot including means for pulling one end of the flexible element away from the other end. The tightening means can form part of the threading means or vice versa. The apparatus can further comprise means for tensioning the flexible element while the latter is being acted upon by the loop forming means; such tensioning means can include a catamenial tampon which is affixed to one end of the flexible element and a suction generating device which exerts a pull upon the other end of the flexible element so that the latter is taut or reasonably taut between the tampon and the intake of the suction generating device.

The loop forming means can include a mandrel and means for convoluting an intermediate portion of the flexible element around the mandrel. If the mandrel is hollow, the threading means can include means for pulling the one end of the flexible element through the mandrel by suction so that the one end passes through the loop which is formed by convoluted material of the flexible element around the mandrel. The tightening means of such apparatus can comprise a pusher, a lever or other suitable means for slipping or stripping the convoluted portion of the flexible element off the mandrel while the pulling means is operative to apply suction to the one end of the flexible element.

A lever or other suitable means can be provided to move the one end of the flexible element into register with the loop preparatory to threading of the one end by the pneumatic threading means; in fact, such moving means can be said to constitute one component of the threading means.

The tensioning means can include means for maintaining the flexible element in a substantially vertical position in the course of loop formation, preferably in such a way that the one end of the flexible element is located at a level below the other end.

If the flexible element has several strands, the loop forming means preferably includes means for substantially simultaneously forming registering closed loops in all strands of the flexible element, the threading means includes means for substantially simultaneously threading one end of each strand through all of the loops, and the tightening means includes means for substantially simultaneously pulling one end of each strand away from the respective other end.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a diagrammatic partly perspective view of a portion of an apparatus which embodies the invention, a flexible element which constitutes the drawstring or a catamenial tampon being shown in a position of readiness for tensioning preparatory to the making of a closed loop;

FIG. 2 illustrates the structure of FIG. 1 in the course of the tensioning step which involves pulling the lower end of the flexible element into a suction port;

FIG. 3 shows the structure of FIG. 2 with the loop forming parts in operative positions;

FIG. 4 shows the structure of FIG. 3 upon completion of the loop forming operation;

FIG. 5 shows the structure of FIG. 4, with the loop forming parts on their way retracted positions;

FIG. 6 illustrates the initial stage of the knot forming step;

FIG. 7 shows the next stage of the knot forming step;

FIG. 8 illustrates a first stage of the knot tightening operation;

FIG. 9 shows the next stage of the knot tightening operation;

FIG. 10 shows the tampon and its drawstring downstream of the knot forming apparatus; and FIG. 11 is a perspective view of a drum-shaped conveyor for the units of the knot forming apparatus and for a flexible carrier of a series of tampons.

DESCRIPTION OF THE PREFERRED EMBODIMENTS

Referring first to FIG. 1, there is shown one of a battery of apparatus each of which serves to form knots 9 (FIGS. 9 and 10) in successive elongated flexible elements 1 each having two strands 15, 16 and each constituting the drawstring of a discrete catamenial tampon 2. The tampons 2 are transported along a predetermined path defined by a flexible carrier 17 which is shown in FIG. 1 and is trained over a conveyor 18 in the form of a drum or the like. Reference may be had to aforementioned commonly owned U.S. Pat. No. 4,302,174 which shows a presently preferred machine for making catamenial tampons. Each tampon 2 is held by a suitable support 19.

The upper end 6 of the flexible element 1 (hereinafter called string for short) which is shown in FIG. 1 forms a knot and is affixed to the respective tampon 2 in a manner not forming part of the invention. The invention resides in the provision of an apparatus for making knots 9 (FIGS. 9-11) in successive strings 1 intermediate their respective upper and lower ends 6, 7. In the first step, the string 1 is tightened so that it extends substantially or exactly vertically (FIG. 2) as a result of the application of suction by way of a port 10 provided in an apertured member 20 which can move with the support 19 in the direction indicated by arrow A in the course of the knot forming operation. Tensioning of the string 1 in a manner as shown in FIG. 2 is desirable and advantageous because this ensures that the string portion between the ends 6, 7 is maintained in a predetermined position with reference to the respective loop forming, knot forming and knot tightening instrumentalities of the illustrated apparatus. The loop forming means of the apparatus includes at least one hollow mandrel 11 which is provided on a housing 21 for a stud or post 12 adjacent the periphery of the mandrel 11 and defining therewith a relatively narrow clearance 22 for an intermediate portion of the string 1 when the latter's lower end 7 is held by suction so that it extends into the port 10. Prior to looping of the string 1, the mandrel 11, its housing 21 and the stud 12 are held in retracted positions which are shown in FIGS. 1 and 2. The housing 21 is then moved forwardly (note the arrow B in FIG. 3) so that the clearance 22 receives a portion of the string 1, and the housing 21 is thereupon rotated (arrow C in FIG. 4) so that a portion of the string 1 is convoluted around the mandrel 11 by the stud 12 and the convoluted portion forms a closed loop 3 between two overlapping portions 4, 5, of the string 1. As a rule, the tampon 2 will remain at the level of FIGS. 1 to 3 so that the making of the closed loop 3 involves extraction of a certain length of the string 1 form the suction port 10 of the apertured member 20 and the closed loop 3 is formed rather close to the lower end 7 of the string.

If desired or necessary, the next step involves a retraction of the housing 21 in the direction of arrow D (FIG. 5) simultaneously with termination of the application of suction to the port 10. This terminates the exertion of a pull upon the lower end 7 so that such lower end can be readily threaded through the closed loop 3 on the mandrel 11 so as to convert the loop into a relatively loose knot. The loop 3 on the mandrel 11 shares the movement of the housing 21 in the direction of arrow D because it is in frictional engagement with the peripheral surface of the mandrel and also because the stud 12 resembles a slightly bent hook which flexes the string 1 in the region of the intermediate portion 5 and thus cooperates with the mandrel 11 in compelling the loop 3 to share the rearward movement of the housing 21.

In the next step, a suitably configured lever 13 is moved from the position of FIG. 1 to the position of FIG. 6 to lift the lower end 7 of the string 1 in front of (i.e., to a position of at least substantial register with) the loop 3 on the mandrel 11, and a suction generating device 8 (FIG. 7) is activated to draw a stream of air into the mandrel 11 (note the arrows E in FIG. 6) so that the inflowing air entrains the end 7 and pulls it into the interior of the hollow mandrel (note FIG. 7). Thus, the lever 13 can be said to constitute a (mechanical) component part of the primarily pneumatic means 8 for threading the end 7 through the loop 3 and to thus complete the conversion of the loop into a knot including the closed loop of FIG. 7 as well as the string portion which extends through such loop in the interior of the mandrel 11.

The lever 13 is then pivoted back to the position of FIG. 1 (see also FIG. 8), and a loop pusher or stripping member 14 is moved forwardly (arrow F in FIG. 8) to strip or slip the loop 3 off the peripheral surface of the mandrel 11 and to thus complete the making of knot in the interior of or behind the mandrel 11.

The knot 9 (FIG. 9) is then tightened as a result of movement of the tampon 2 and the upper end 6 of the string 1 in the direction of arrow A as well as due to continued application of suction to the lower end 7 of the string, i.e., the string 1 remains taut between its ends 6 and 7 so that the size of the loop 3 diminishes and the knot 9 assumes its ultimate shape which is determined by the resistance offered by the suction generating device 8 to extraction of the knot 9 from the interior of the mandrel 11. By properly synchronizing the movements of the support 19, the housing 21, lever 13 and pusher 14 with the application of suction to the port 10 and (by 8) to the interior of the mandrel 11, one ensures that each and every string 1 of a long series of strings will be provided with a knot 9 of identical size and shape as well as at the same distance from the end 7.

The stud 12 loops both strands 15, 16 of the string 1 simultaneously so as to form a closed loop 3 which is actually a combination of two overlapping loops, and the threading of the lower ends of both strands 15, 16 also takes place simultaneously under the action of the lever 13 and suction generating device 8. Furthermore, the pusher 14 strips both loops off the mandrel 11 in a simultaneous step so that the two strands 15, 16 are manipulated as if they were a single strand.

FIG. 10 shows the knot 9 in its final form at the desired level beneath the end 6 which is attached to the respective tampon 2. The purpose of the knot 9 is to facilitate manipulation of the tampon 2 during extraction from the body cavity as well as during disposal. Similar knots can be formed in other types of strings, e.g., in the strings of tea bags, in shoe laces, in the pull strings for zippers and for many other applications where flexible elements are to be provided with knots at predetermined locations and at a high frequency such as is required in a mass-producing machine or production line to avoid bottlenecks at the knot forming station.

The illustrated apparatus consitutes one of an entire annulus of preferably identical apparatus which are mounted on the rotary drum-shaped conveyor 18 of FIG. 11 and are designed to treat a series of successively delivered strings 1 in a tampon making or other machine.

The exact construction of the means for reciprocating the housing 21 for the mandrel 11 and stud 12 forms no part of the invention. For example, each housing 11 can be provided with a roller follower extending into the groove of a stationary cam 24 (indicated in FIG. 11 by a broken-line circle) so that the housing 21 moves forwardly and backwards during predetermined stages of each revolution about the axis of its drum-shaped conveyor 18. The suction generating device 8 is installed in the interior of the conveyor 18 and its suction intake communicates with the axial passages of successive mandrels 11 during certain stages of each revolution of the conveyor. Each lever 13 can be pivoted by a second cam in the conveyor 18, and a further cam 18 in the conveyor is used to move the pusher 14 forwardly and backwards in parallelism with the axis of the respective housing 21 during each revolution of the conveyor 18. Any other suitable means (e.g., fluid-operated motors or the like) can be used in lieu of a set of cams to rotate the housing 21, to pivot the lever 13 and to reciprocate the pusher 14 at required intervals so as to ensure the making of identical knots 9 in each of a relatively short or long series of successive strings 1. Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for making a knot in an elongated flexible element, such as the drawstring of a catamenial tampon, comprising means for forming in the element a closed loop between the ends of the element, including means for overlapping two intermediate portions of the element; means for pneumatically threading one end of the element through the loop to thus form a relatively loose knot; and means for tightening the knot, including means for pulling one end of the element away from the other end until the loop closely surrounds an intermediate portion of the element.

2. The apparatus of claim 1, wherein one of said tightening and threading means forms part of the other of said tightening and threading means.

3. The apparatus of claim 1, further comprising means for tensioning the element while the element is being acted upon by said loop forming means.

4. The apparatus of claim 1, wherein said loop forming means includes a mandrel and means for convoluting the element around said mandrel.

5. The apparatus of claim 4, wherein said mandrel is hollow and said threading means includes means for pulling the one end of the element through the mandrel by suction.

6. The apparatus of claim 5, wherein said tightening means includes means for slipping the convoluted portion of the element off said mandrel while said pulling means is operative to apply suction to the one end of the element.

7. The apparatus of claim 1, further comprising means for moving the one end of the element into register with the loop preparatory to threading of the one end by said pneumatic means.

8. The apparatus of claim 1, further comprising means for maintaining the element in a substantially upright position in the course of the loop formation so that the one end of the element is located at a level below the other end thereof.

9. The apparatus of claim 1 for making a knot in a multi-strand flexible element, wherein said loop forming means includes means for substantially simultaneously forming registering closed loops in all strands of the element, said threading means including means for substantially simultaneously threading one end of each strand through all of the closed loops and said tightening means including means for substantially simultaneously pulling one end of each strand away from the other end.

* * * * *